(12) United States Patent
Schelhaas et al.

(10) Patent No.: US 6,706,924 B2
(45) Date of Patent: Mar. 16, 2004

(54) PROCESS FOR THE PRODUCTION OF 1,5-NAPHTHALENEDIAMINE

(75) Inventors: Michael Schelhaas, Köln (DE); Katrin Joschek, Köln (DE); Manfred Jautelat, Burscheid (DE); Joachim Zechlin, Düsseldorf (DE); Dietmar Wastian, Dormagen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 209 days.

(21) Appl. No.: 10/028,892

(22) Filed: Dec. 18, 2001

(65) Prior Publication Data

US 2002/0103401 A1 Aug. 1, 2002

(30) Foreign Application Priority Data

Dec. 22, 2000 (DE) .......................... 100 64 779
Oct. 5, 2001 (DE) .......................... 101 49 041

(51) Int. Cl.$^7$ ...................... C07C 211/58; C07C 209/60
(52) U.S. Cl. ...................... 564/305; 564/416
(58) Field of Search ................. 564/305, 416

(56) References Cited

U.S. PATENT DOCUMENTS 4,973,758 A 11/1990 Behre et al. ................ 564/394

FOREIGN PATENT DOCUMENTS

| GB | 1499699 | 2/1978 |
|---|---|---|
| JP | 56-59738 | 5/1981 |
| JP | 4-154745 | 5/1992 |

OTHER PUBLICATIONS

Cameron et al, Aust. J. Chem., vol 29, pp. 2499–2509, 1976.*

Nomenclature of Inorganic Chemistry Recommendation (month unavailable) 1990, Chapter 1–3.8.1 pp. 41–43, Groups of element in the Periodic Table and their subdivisions, edited by G.J. Leigh.

Ullmann's Encyclopedia of Industrial Chemistry, 5$^{th}$ ed., vol. A A13 (month unavailable) 1989, pp. 487–497, Hydrogenation and Dehydrogenation, Paul N. Rylander.

Ohira, Noriyuki et al: "Organotellurims. Part IV. Reduction of aromatic nitro compounds to amines by benzenetellurol" Chem. Lett. (1984), (6), 853–4, XP002198319 * Run 14, 16, in Tabelle 1, Seite 85 *.

* J. Bornstein et al: "The synthesis of alpha–amino–o–toluidehyde diethylacetal and its attemted Conversion to pseudoindole" Journal of the American Chemical Society., vol. 78, No. 1, 1956, pp. 83–36, XP002148447.

*E. Bellasio et al: "The reaction of Phthalazino '2,3–b! phthalazine–t, 12(H, 14H)–diones with nitrous acid" Farmaco, Edizione Scientifica, vol. 30, No. 5, 1975, pp. 343–352, XP002148448, Societa Chimica Italiana, Pavia., IT.

Römpp Lexikon Chemie; Georg Thieme Verlag, Stuttgart, 10$^{th}$ edition, (month unavailable) 1997, pp. 891–892 "Dehydrierung" and pp. 1831–1832 "Hydrinden".

* cited by examiner

Primary Examiner—Shailendra Kumar
(74) Attorney, Agent, or Firm—Joseph C. Gil

(57) ABSTRACT

The invention relates to a process for the production of 1,5-naphthalenediamine and to the intermediates 4-(2-nitrophenyl)butyronitrile, 5-nitro-3,4-dihydro-1(2H)-naphthyl-imine, 5-nitroso-1-naphthylamine, 5-nitro-1-naphthylamine, 4-(2-aminophenyl)-butyronitrile, 5-amino-3,4-dihydro-1(2H)-naphthalene imine, 4-(2-nitrophenyl) ethyl butyrate and 4-(2-nitrophenyl)butyramide obtainable during the process.

11 Claims, No Drawings

PROCESS FOR THE PRODUCTION OF 1,5-NAPHTHALENEDIAMINE

The invention relates to a process for the production of 1,5-naphthalenediamine by the reaction of ortho-nitrotoluene with an acrylic acid derivative, and to the intermediate products 4-(2-nitrophenyl)butyronitrile, 5-nitro-3,4-dihydro-1(2H)-naphthylimine, 5-nitroso-1-naphthylamine, 5-nitro-1-naphthylamine, 4-(2-aminophenyl)butyronitrile, 4-(2-nitrophenyl)ethyl butyrate, 4-(2-nitrophenyl)butyl butyrate, 4-(2-nitrophenyl)-butyramide and 5-amino-3,4-dihydro-1(2H)-naphthalene imine obtainable during the process.

Various processes for the production of 1,5-naphthalenediamine are already known in the literature. In general, the preparation of 1,5-naphthalenediamine starts from naphthalene which is suitably substituted. Thus, in JP-A2-07 278 066, the synthesis of 1,5-naphthalenediamine via an amine-bromine exchange on 1,5-bromoamino-naphthalene is described. The required educt is produced by bromination of 1-nitronaphthalene in this process.

In JP-A2-04 154 745, JP-A2-56 059 738 and DE-A1-2 523 351, the synthesis of 1,5-naphthalenediamine in combination with 1,8-naphthalenediamine by the reduction of a mixture of 1,5- and 1,8-dinitronaphthalene is described. In DE-C1-3 840 618, the synthesis of 1,5-naphthalenediamine by alkaline hydrolysis of disodium naphthalene-1,5-disulfonate and subsequent reaction with ammonia is described.

All these processes have the disadvantage that the product, or an intermediate produced during the process, is obtained as a mixture of isomers containing other isomers in addition to the 1,5 isomer, which have to be separated off. In addition, the process described in DE-C1-3 840 618 in particular takes place under very severe and corrosive reaction conditions.

The object of the present invention is therefore to provide a simple process for the production of 1,5-naphthalenediamine, by which 1,5-naphthalenediamine can be produced in just a few steps, starting from basic chemicals, without other isomers forming in significant quantities and having to be separated off.

A process has now been found, by which 1,5-naphthalenediamine can be prepared simply, in just a few steps and largely as a pure isomer, starting from ortho-nitrotoluene and acrylic acid derivatives, such as e.g. acrylonitrile, two inexpensive basic chemicals.

The object is achieved according to the invention by a process for the production of 1,5-naphthalenediamine containing a step in which ortho-nitrotoluene is reacted with an acrylic acid derivative.

Preferred acrylic acid derivatives are acrylic acid esters, such as e.g. methyl acrylate and ethyl acrylate, acrylamide and acrylonitrile.

The object is achieved according to the invention in particular by a process for the production of 1,5-naphthalenediamine containing a step in which ortho-nitrotoluene is reacted with acrylonitrile to give 4-(2-nitrophenyl)butyronitrile.

In a first preferred embodiment, the process for the production of 1,5-naphthalene-diamine contains the following steps:

a) reaction of ortho-nitrotoluene with acrylonitrile to give 4-(2-nitrophenyl)-butyronitrile,
b) cyclisation of the 4-(2-nitrophenyl)butyronitrile formed in step a) to the nitro imine and/or nitro enamine,
c) aromatisation of the nitro imine and/or nitro enamine formed in step b) to give 5-nitro-1-naphthylamine and/or 5-nitroso-1-naphthylamine,
d) hydrogenation of the 5-nitro-1-naphthylamine and/or 5-nitroso-1-naphthylamine formed in step c) to give 1,5-naphthalenediamine.

4-(2-Nitrophenyl)butyronitrile is produced from ortho-nitrotoluene and acrylonitrile preferably at temperatures of −10° C. to 100° C. It is particularly preferred to operate at 20° C. to 75° C., especially preferably at temperatures of 30° C. to 60° C.

The reaction is performed with base catalysis. Oxides, hydroxides and carbonates of lithium, sodium, potassium, rubidium, caesium, magnesium, calcium, strontium, barium or aluminium, and mixtures thereof, can be used as bases. Sodium hydroxide and potassium hydroxide are particularly suitable. In a preferred embodiment, the aqueous solutions are used in combination with a phase transfer catalyst. These phase transfer catalysts are e.g. quaternary ammonium salts. Suitable ammonium compounds are tetraalkylammonium halides and hydrogen sulfates, such as tributylmethyl-ammonium chloride, trioctylammonium chloride, tetrabutylammonium chloride or tetrabutylammonium hydrogen sulfate. The use of appropriate tetraalkyl- or tetraarylphosphonium salts, such as tetramethylphosphonium bromide and tetraphenyl-phosphonium bromide is also suitable, as is the use of solubility promoters, such as polyethylene glycol dimethyl ethers.

In principle, water and all organic solvents that are stable in bases are suitable as the solvents. Aromatic solvents, such as benzene, toluene, xylene, chlorobenzene, nitrobenzene or nitrotoluene, and also dimethyl sulfoxide, dimethyl formamide and aliphatic hydrocarbons, such as ligroin, cyclohexane, pentane, hexane, heptane or octane, are preferably used.

ortho-Nitrotoluene is particularly preferably used as educt and, at the same time, as solvent, and in an excess of ortho-nitrotoluene of 1 to 40 equivalents, especially 5 to 20 equivalents, based on acrylonitrile.

The cyclisation of 4-(2-nitrophenyl)butyronitrile to 5-nitro-3,4-dihydro-1-naphthylamine or the tautomeric 5-nitro-3,4-dihydro-1(2H)-naphthylimine is performed in substance or in an inert solvent in the presence of strong acids. Suitable solvents are linear, branched or cyclic aliphatic hydrocarbons, such as ligroin or cyclohexane, pentane, hexane, heptane, octane and aromatic solvents such as nitrotoluene. It is preferred to operate in substance or in ortho-nitrotoluene.

Suitable acids are strong Lewis or Bronsted acids, such as e.g. aluminium chloride, boron trifluoride, sulfuric acid, phosphoric acid, polyphosphoric acid, phosphorus pentoxide, methanesulfonic acid, trifluoromethanesulfonic acid, trifluoroacetic acid or mixtures of antimony pentafluoride and fluorosulfuric acid. Mixtures of the acids can also be used.

The acid is generally used in 0.1 to 100 mole equivalents, based on 4-(2-nitrophenyl)-butyronitrile. Preferably, 0.5 to 20 equivalents are used, particularly preferably 1 to 10 equivalents.

The reaction is generally carried out at temperatures of 0° C. to 200° C., preferably between 40° C. and 150° C., particularly preferably between 60° C. and 110° C.

The nitro imine and/or nitro enamine formed in step b), which is sensitive to hydrolysis, is preferably first converted to the nitroketone 5-nitro-3,4-dihydro-1(2H)-naphthalenone, e.g. by hydrolysis, and the nitroketone is isolated. The isolation takes place e.g. by phase separation.

The nitroketone is then converted back to the nitro imine and/or nitro enamine in step c) by reaction with ammonia, preferably in the presence of ammonium salts such as ammonium chloride, and then aromatised. The aromatisation then preferably takes place in ammonia as the solvent.

The aromatisation or dehydrogenation of the nitro enamine 5-nitro-3,4-dihydro-1-naphthylamine or of the nitro imine 5-nitro-3,4-dihydro-1(2H)-naphthylimine to 5-nitro-1-naphthylamine or 5-nitroso-1-naphthylamine or a mixture of the compounds is carried out, e.g. in an inert solvent, in the presence of a catalyst. In addition to the dehydrogenated product 5-nitro-1-naphthylamine, 5-nitroso-1-naphthylamine formally resulting from symproportionation can also be produced in the process. 1,5-Naphthalenediamine is also formed in traces. The products can be further processed in any mixing ratios. Suitable solvents are ammonia and linear, branched or cyclic aliphatic hydrocarbons such as ligroin or cyclohexane, and also acetonitrile and aromatic solvents such as benzene, toluene, xylene, nitrobenzene, nitrotoluene or chlorobenzene. The aromatisation can also be performed in the absence of a solvent.

Suitable catalysts are dehydrogenation catalysts, which are described in the literature (Römpp Lexikon Chemie; Georg Thieme Verlag, Stuttgart, 10$^{th}$ edition 1997, p. 891, chapter "Dehydrierung", 1$^{st}$ section; Ullmann's Encyclopedia of Industrial Chemistry, VCH Verlagsgesellschaft mbH, Weinheim, 5$^{th}$ edition 1989, vol. A13, chapter "Hydrogenation and Dehydrogenation", sub-chapter 2, "Dehydrogenation", p. 494–497). These include the metals of groups 8–10 of the periodic table (G. J. Leigh [editor], Nomenclature of Inorganic Chemistry, Recommendations 1990, Blackwell Scientific Publications, Oxford, Chapter I-3.8.1 "Groups of Elements in the Periodic Table and their Subdivision, p. 41–43), especially platinum, palladium, ruthenium and iridium, iron, cobalt, nickel and combinations thereof. The metals can also be used together with other metals, such as lanthanum, scandium, vanadium, chromium, molybdenum, tungsten, manganese, tin, zinc, copper, silver or indium. The above metals can be present as pure elements, as oxides, sulfides, halides, carbides or nitrides or can be used in combination with organic ligands. Suitable as ligands are hydrocarbon compounds with donor groups, such as e.g. amines, nitrites, phosphines, thiols, thioethers, alcohols, ethers or carboxylic acids. The catalysts are optionally applied to a support material. Suitable support materials are activated charcoal, aluminium oxide, silicon dioxide, zirconium oxide, zinc oxide or zeolites.

Work is optionally performed in the presence of an oxidising agent such as oxygen or air. The reaction is generally carried out at temperatures of 50° C. to 250° C., preferably at 100° C. to 200° C.

The reduction of the nitro group to the product 1,5-naphthalenediamine takes place by hydrogenation in the presence of suitable hydrogenation catalysts.

Practically all heterogeneous catalysts that are known as hydrogenation catalysts are suitable as hydrogenation catalysts for the process according to the invention (Römpp Lexikon Chemie; Georg Thieme Verlag, Stuttgart, 10$^{th}$ edition 1997, p. 1831, chapter "Hydrierung"; Ullmann's Encyclopedia of Industrial Chemistry, VCH Verlagsgesellschaft mbH, Weinheim, 5$^{th}$ edition 1989, vol. A13, chapter "Hydrogenation and Dehydrogenation", sub-chapter 1.2 "Catalysts", p. 488). Preferred catalysts are the metals of groups 8–10 of the periodic table (G. J. Leigh [editor], Nomenclature of Inorganic Chemistry, Recommendations 1990, Blackwell Scientific Publications, Oxford, Chapter I-3.8.1 "Groups of Elements in the Periodic Table and their Subdivision, p. 41–43), copper or chromium on a suitable support with a metal content of 0.01 to 50 wt. %, preferably 0.1 to 20 wt. %, based on the total weight of the catalyst. Catalysts containing one or more of the above-mentioned metals can also be used. Preferred metals are, in particular, platinum, palladium and rhodium, platinum and palladium being particularly preferred. Other preferred catalysts are Raney nickel and supported nickel catalysts. The above-mentioned metals or their compounds can also be used in pure form as a solid. Palladium black and platinum black can be mentioned as examples of a metal in pure form.

The catalysts can be used in batchwise process variants in quantities of 0.01 to 50 wt. %, based on 5-nitro- or 5-nitroso-1-naphthylamine used, preferably in quantities of 0.01 to 20 wt. %, particularly preferably in quantities of 0.01 to 10 wt. %. When the reaction is carried out continuously, for example in a stirred vessel with powdered catalyst or in the trickle phase on a fixed bed catalyst, loads of 0.01 to 500 g, preferably 0.1 to 200 g, particularly preferably 1 to 100 g of 5-nitro- or 5-nitroso-1-naphthylamine per g catalyst per hour can be set.

The reaction temperatures are generally −20° C. to 150° C., particularly −10° C. to 80° C.; the hydrogen pressure is generally 0.1 to 150 bar, particularly 0.5 to 70 bar, especially preferably 1 to 50 bar.

The same catalyst is preferably used for the aromatisation and the subsequent hydrogenation, it being possible for the two steps to be performed in one reaction vessel.

All the reaction steps in this preferred embodiment of the process can be carried out continuously or batchwise, e.g. in stirred vessel reactors or tubular reactors.

In a second preferred embodiment, the process for the production of 1,5-naphthalenediamine contains the steps a) reaction of ortho-nitrotoluene with acrylonitrile to give 4-(2-nitrophenyl)-butyronitrile, b) reduction of the 4-(2-nitrophenyl)butyronitrile formed in step a) to give 4-(2-aminophenyl)butyronitrile, c) cyclisation of the 4-(2-aminophenyl)butyronitrile formed in step b) to the amino imine and/or amino enamine, d) aromatisation of the amino imine and/or amino enamine formed in step c) to give 1,5-naphthalenediamine.

4-(2-Nitrophenyl)butyronitrile is prepared from ortho-nitrotoluene and acrylonitrile as in step a) of the first preferred embodiment.

This compound is then reduced to 4-(2-aminophenyl) butyronitrile. The transformation can be performed by hydrogenation in the presence of a hydrogenation catalyst. Practically all heterogeneous catalysts that are known as hydrogenation catalysts are suitable as hydrogenation catalysts for the process according to the invention (Römpp Lexikon Chemie; Georg Thieme Verlag, Stuttgart, 10$^{th}$ edition 1997, p. 1831, chapter "Hydrierung"; Ullmann's Encyclopedia of Industrial Chemistry, VCH Verlagsgesellschaft mbH, Weinheim, 5$^{th}$ edition 1989, vol. A13, chapter "Hydrogenation and Dehydrogenation", sub-chapter 1.2 "Catalysts", p. 488). Preferred catalysts are the metals of groups 8–10 of the periodic table (G. J. Leigh [editor], Nomenclature of Inorganic Chemistry, Recommendations 1990, Blackwell Scientific Publications, Oxford, Chapter I-3.8.1 "Groups of Elements in the Periodic Table and their Subdivision, p. 41–43), copper or chromium on a suitable support with a metal content of 0.01 to 50 wt. %, preferably 0.1 to 20 wt. %, based on the total weight of the catalyst. Catalysts containing one or more of the above-mentioned metals can also be used. Preferred metals are, in particular, platinum, palladium and rhodium, platinum and palladium being particularly preferred. Other preferred catalysts are Raney nickel and supported nickel catalysts. The above-mentioned metals or their compounds can also be used in pure form as a solid. Palladium black and platinum black can be mentioned as examples of a metal in pure form.

In another embodiment, the nitro group can be reduced by reaction with metal hydrides, optionally with the addition of additives, or by reaction with base metals such as iron.

Preferred metal hydrides are sodium borohydride, potassium borohydride, lithium borohydride, sodium cyanoborohydride, lithium cyanoborohydride, lithium aluminium hydride and diisobutylaluminium hydride. Suitable additives are nickel salts, tellurium compounds and antimony compounds.

Preferred base metals for the reaction under acid conditions are iron, zinc, magnesium, aluminium and tin, iron and zinc being particularly preferred. Suitable solvents for this purpose are water or alcohols or mixtures of alcohols acidified with acids such as acetic acid, hydrochloric acid, sulfuric acid or ammonium chloride. Suitable alcohols are methanol, ethanol, n-propanol, isopropanol, n-butanol, sec.-butanol, tert.-butanol or cyclohexanol. Methanol and ethanol are particularly preferred.

The cyclisation to 5-amino-3,4-dihydro-1-naphthylamine or the imine tautomer 5-amino-3,4-dihydro-1(2H)-naphthylimine is performed in the same way as the cyclisation of the nitro compound (step b in the first preferred embodiment). However, owing to the basicity of the amino group in 4-(2-aminophenyl)butyronitrile, at least one mole equivalent of acid (based on 4-(2-aminophenyl) butyronitrile) must also be added. Preferably, 1.5 to 21 equivalents of acid are used, particularly preferably 1.5 to 11 equivalents.

The reaction is carried out in substance or in an inert solvent in the presence of strong acids. Suitable solvents are linear, branched or cyclic aliphatic hydrocarbons, such as ligroin or cyclohexane, pentane, hexane, heptane, octane and aromatic solvents such as nitrotoluene. It is preferred to work in substance or in ortho-nitrotoluene.

Suitable acids are strong Lewis or Bronsted acids, such as e.g. aluminium chloride, boron trifluoride, sulfuric acid, phosphoric acid, polyphosphoric acid, phosphorus pentoxide, methanesulfonic acid, trifluoromethanesulfonic acid, trifluoroacetic acid or mixtures of antimony pentafluoride and fluorosulfuric acid. Mixtures of the acids can also be used.

The reaction is generally carried out at temperatures of 0° C. to 150° C., preferably between 60° C. and 110° C.

After the cyclisation, the reaction mixture is conventionally neutralised. This is achieved e.g. by adding sodium hydroxide solution.

The amino imine and/or amino enamine formed in step c) is preferably first converted to the aminoketone 5-amino-3,4-dihydro-1(2H)-naphthalenone, e.g. by hydrolysis, and the aminoketone is isolated. The isolation takes place e.g. by phase separation. The aminoketone is then converted back to the amino imine and/or amino enamine in step d) by reaction with ammonia, preferably in the presence of ammonium chloride, and then aromatised. The aromatisation then preferably takes place in ammonia.

The aromatisation of 5-amino-3,4-dihydro-1-naphthylamine or the imine tautomer 5-amino-3,4-dihydro-1(2H)-naphthylimine to 1,5-naphthalenediamine is performed in the same way as the aromatisation of the nitro compounds 5-nitro-3,4-dihydro-1-naphthyl-amine or 5-nitro-3,4-dihydro-1(2H)-naphthylimine (step c) of the first preferred embodiment).

The reaction is carried out in an inert solvent in the presence of a catalyst. Suitable solvents are ammonia and linear, branched or cyclic aliphatic hydrocarbons, such as ligroin or cyclohexane, and also acetonitrile and aromatic solvents such as benzene, toluene, xylene, nitrobenzene, nitrotoluene or chlorobenzene.

Suitable catalysts are dehydrogenation catalysts, which are described in the literature (Römpp Lexikon Chemie; Georg Thieme Verlag, Stuttgart, $10^{th}$ edition 1997, p. 891, chapter "Dehydrierung", $1^{st}$ section; Ullmann's Encyclopedia of Industrial Chemistry, VCH Verlagsgesellschaft mbH, Weinheim, $5^{th}$ edition 1989, vol. A13, chapter "Hydrogenation and Dehydrogenation", sub-chapter 2, "Dehydrogenation", p. 494–497). These include the metals of groups 8–10 of the periodic table (G. J. Leigh [editor], Nomenclature of Inorganic Chemistry, Recommendations 1990, Blackwell Scientific Publications, Oxford, Chapter I-3.8.1 "Groups of Elements in the Periodic Table and their Subdivision, p. 41–43), especially platinum, palladium, ruthenium and iridium, iron, cobalt, nickel and combinations thereof. The metals can also be used together with other metals, such as lanthanum, scandium, vanadium, chromium, molybdenum, tungsten, manganese, tin, zinc, copper, silver or indium. The above metals can be present as pure elements, as oxides, sulfides, halides, carbides or nitrides or can be used in combination with organic ligands. Suitable as ligands are hydrocarbon compounds with donor groups such as e.g. amines, nitrites, phosphines, thiols, thioethers, alcohols, ethers or carboxylic acids. The catalysts are optionally applied to a support material. Suitable support materials are activated charcoal, aluminium oxide, silicon dioxide, zirconium oxide, zinc oxide or zeolites.

Work is optionally performed in the presence of an oxidising agent such as oxygen or air.

The reaction is generally carried out at temperatures of 50° C. to 250° C., preferably at 100° C. to 200° C.

All the reaction steps in this preferred embodiment of the process can be performed continuously or batchwise, e.g. in stirred vessel reactors or tubular reactors.

In a third preferred embodiment, the process for the production of 1,5-naphthalene-diamine contains the steps a) reaction of ortho-nitrotoluene with acrylonitrile to give 4-(2-nitrophenyl)-butyronitrile, b) cyclisation of the 4-(2-nitrophenyl)butyronitrile formed in step a) to the nitro imine and/or nitro enamine, c) reduction of the nitro imine and/or nitro enamine formed in step b) to give the amino imine and/or amino enamine, d) aromatisation of the amino imine and/or amino enamine formed in step c) to give 1,5-naphthalenediamine. 4-(2-Nitrophenyl)butyronitrile is prepared from ortho-nitrotoluene and acrylonitrile in the same way as in step a) of the first preferred embodiment.

This compound is then cyclised to give 5-nitro-3,4-dihydro-1-naphthylamine or the tautomeric 5-nitro-3,4-dihydro-1(2H)-naphthylimine in the same way as in step b) of the first preferred embodiment.

The compound 5-nitro-3,4-dihydro-1-naphthylamine or the tautomeric 5-nitro-3,4-dihydro-1(2H)-naphthylimine is now reduced to give 5-amino-3,4-dihydro-1-naphthyl-amine or the tautomeric 5-amino-3,4-dihydro-1(2H)-naphthylimine.

The transformation can be performed by hydrogenation in the presence of a hydrogenation catalyst. Practically all heterogeneous catalysts that are known as hydrogenation catalysts are suitable as hydrogenation catalysts for the process according to the invention (Römpp Lexikon Chemie; Georg Theme Verlag, Stuttgart, 10$^{th}$ edition 1997, p. 1831, chapter "Hydrierung"; Ullmann's Encyclopedia of Industrial Chemistry, VCH Verlagsgesellschaft mbH, Weinheim, 5$^{th}$ edition 1989, vol. A13, chapter "Hydrogenation and Dehydrogenation", sub-chapter 1.2 "Catalysts", p. 488). Preferred catalysts are the metals of groups 8–10 of the periodic table (G. J. Leigh [editor], Nomenclature of Inorganic Chemistry, Recommendations 1990, Blackwell Scientific Publications, Oxford, Chapter I-3.8.1 "Groups of Elements in the Periodic Table and their Subdivision, p. 41–43), copper or chromium on a suitable support with, a metal content of 0.01 to 50 wt. %, preferably 0.1 to 20 wt. %, based on the total weight of the catalyst. Catalysts containing one or more of the above-mentioned metals can also be used. Preferred metals are, in particular, platinum, palladium and rhodium, platinum and palladium being particularly preferred. Other preferred catalysts are Raney nickel and supported nickel catalysts. The above-mentioned metals or their compounds can also be used in pure form as a solid. Palladium black and platinum black can be mentioned as examples of a metal in pure form.

The final aromatisation of 5-amino-3,4-dihydro-1-naphthylamine or the tautomeric 5-amino-3,4-dihydro-1(2H)-naphthylimine to 1,5-naphthalenediamine is performed in the same way as in step d) of the second preferred embodiment.

All the reaction steps in this preferred embodiment of the process can be carried out continuously or batchwise, e.g. in stirred vessel reactors or tubular reactors.

In a fourth preferred embodiment the process for the production of 1,5-naphthalenediamine contains the steps:

a) reaction of ortho-nitrotoluene with acrylonitrile to give 4-(2-nitrophenyl)-butyronitrile, b) cyclisation of the 4-(2-nitrophenyl)butyronitrile formed in step a) to the nitro imine and/or nitro enamine, conversion to the nitroketone 5-nitro-3,4-dihydro-1(2H)-naphthalenone, and isolation of the nitroketone, c) reduction of the nitroketone formed in step b) to give the aminoketone 5-amino-3,4-dihydro-1(2H)-naphthalenone, d) conversion of the aminoketone formed in step c) to the amino imine and/or amino enamine and aromatisation to give 1,5-naphthalenediamine.

4-(2-Nitrophenyl)butyronitrile is prepared from ortho-nitrotoluene and acrylonitrile in the same way as in step a) of the first preferred embodiment.

4-(2-Nitrophenyl)butyronitrile is then cyclised to 5-nitro-3,4-dihydro-1-naphthylamine or the tautomeric 5-nitro-3,4-dihydro-1(2H)-naphthylimine as in step b) of the first preferred embodiment. The 5-nitro-3,4-dihydro-1-naphthylamine and/or 5-nitro-3,4-dihydro-1(2H)-naphthylimine is then converted to the nitroketone 5-nitro-3,4-dihydro-1(2H)-naphthalenone, e.g. by hydrolysis, and the nitroketone is isolated. The isolation of the nitroketone takes place e.g. by phase separation.

The compound 5-nitro-3,4-dihydro-1(2H)-naphthalenone is now reduced to give 5-amino-3,4-dihydro-1(2H)-naphthalenone.

The transformation can be performed by hydrogenation in the presence of a hydrogenation catalyst. Practically all heterogeneous catalysts that are known as hydrogenation catalysts are suitable as hydrogenation catalysts for the process according to the invention (Römpp Lexikon Chemie; Georg Thieme Verlag, Stuttgart, 10$^{th}$ edition 1997, p. 1831, chapter "Hydrierung"; Ullmann's Encyclopedia of Industrial Chemistry, VCH Verlagsgesellschaft mbH, Weinheim, 5$^{th}$ edition 1989, vol. A13, chapter "Hydrogenation and Dehydrogenation", sub-chapter 1.2 "Catalysts", p. 488). Preferred catalysts are the metals of groups 8–10 of the periodic table (G. J. Leigh [editor], Nomenclature of Inorganic Chemistry, Recommendations 1990, Blackwell Scientific Publications, Oxford, Chapter I-3.8.1 "Groups of Elements in the Periodic Table and their Subdivision, p. 41–43), or copper and/or chromium on a suitable support with a metal content of 0.01 to 50 wt. %, preferably 0.1 to 20 wt. %, based on the total weight of the catalyst. Catalysts containing one or more of the above-mentioned metals can also be used. Preferred metals are, in particular, platinum, palladium and rhodium, platinum and palladium being particularly preferred. Other preferred catalysts are Raney nickel and supported nickel catalysts. The above-mentioned metals or their compounds can also be used in pure form as a solid. Palladium black and platinum black can be mentioned as examples of a metal in pure form.

The 5-amino-3,4-dihydro-1(2H)-naphthalenone produced in the reduction is then converted to 5-amino-3,4-dihydro-1-naphthylamine and/or 5-amino-3,4-dihydro-1(2H)-naphthylimine by reacting with ammonia, preferably in the presence of ammonium chloride.

The final aromatisation of 5-amino-3,4-dihydro-1-naphthylamine and/or the tautomeric 5-amino-3,4-dihydro-1(2H)-naphthylimine to 1,5-naphthalenediamine is performed as in step d) of the second preferred embodiment.

The conversion of the 5-amino-3,4-dihydro-1(2H)-naphthalenone to 5-amino-3,4-dihydro-1-naphthylamine and/or 5-amino-3,4-dihydro-1(2H)-naphthylimine and the subsequent aromatisation are preferably carried out in one reaction vessel.

All the reaction steps in this preferred embodiment of the process can be performed continuously or batchwise, e.g. in stirred vessel reactors or tubular reactors.

The processes according to the invention based on ortho-nitrotoluene and acrylonitrile can be illustrated in idealised form by the following reaction diagram:

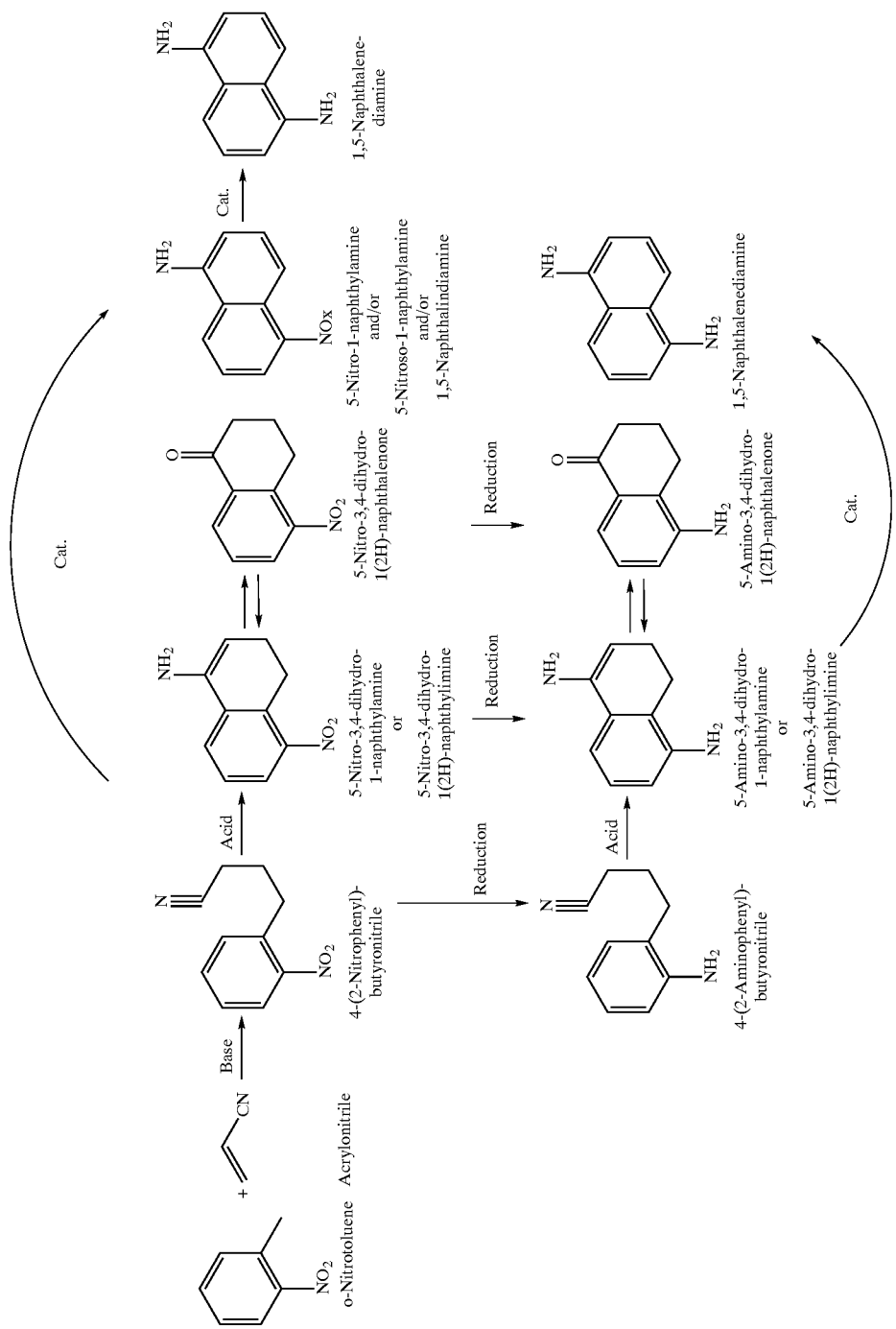

In a fifth preferred embodiment, the process for the production of 1,5-naphthalene-diamine contains the steps:
a) reaction of ortho-nitrotoluene with an acrylate or acrylamide to give 4-(2-nitrophenyl)butyrate or 4-(2-nitrophenyl)butyramide,
b) cyclisation of the butyrate or butyramide formed in step a) to give 5-nitro-3,4-dihydro-1(2H)-naphthalenone,
c) amination of the 5-nitro-3,4-dihydro-1(2H)-naphthalenone formed in step b) to give 5-nitro-3,4-dihydro-1-naphthylamine or the tautomeric 5-nitro-3,4-dihydro-1(2H)-naphthylimine,
d) aromatisation of the 5-nitro-3,4-dihydro-1-naphthylamine or the tautomeric 5-nitro-3,4-dihydro-1(2H)-naphthylimine formed in step c) to give 5-nitro-1-naphthylamine and/or 5-nitroso-1-naphthylamine,
e) hydrogenation of the 5-nitro-1-naphthylamine and/or 5-nitroso-1-naphthylamine formed in step d) to give 1,5-naphthalenediamine.

4-(2-Nitrophenyl)butyrates or 4-(2-nitrophenyl)butyramides are produced from ortho-nitrotoluene and acrylates or acrylamides preferably at temperatures of −10° C. to 100° C., It is particularly preferred to work at 20° C. to 75° C., especially preferably at temperatures of 30° C. to 60° C.

The reaction is performed with base catalysis. Oxides, hydroxides and carbonates of lithium, sodium, potassium, rubidium, caesium, magnesium, calcium, strontium, barium or aluminium, and mixtures thereof, can be used as bases. Sodium hydroxide and potassium hydroxide are particularly suitable. In a preferred embodiment, the aqueous solutions are used in combination with a phase transfer catalyst. These phase transfer catalysts are e.g. quaternary ammonium salts. Suitable ammonium compounds are tetraalkylammonium halides and hydrogen sulfates, such as tributylmethylammonium chloride, trioctylammonium chloride, tetrabutylammonium chloride or tetrabutylammonium hydrogen sulfate. The use of appropriate tetraalkyl- or tetraarylphosphonium salts, such as tetramethylphosphonium bromide and tetraphenyl-phosphonium bromide is also suitable, as is the use of solubility promoters, such as polyethylene glycol dimethyl ethers.

In principle, water and all organic solvents that are stable in bases are suitable as the solvents. Aromatic solvents, such as benzene, toluene, xylene, chlorobenzene, nitrobenzene or nitrotoluene, and also dimethyl sulfoxide, dimethyl formamide and aliphatic hydrocarbons, such as ligroin, cyclohexane, pentane, hexane, heptane or octane, are preferably used.

ortho-Nitrotoluene is particularly preferably used as educt and, at the same time, as solvent, and in an excess of ortho-nitrotoluene of 1 to 40 equivalents, especially 5 to 20 equivalents, based on the acrylic acid derivative.

The cyclisation of 4-(2-nitrophenyl)butyrates or 4-(2-nitrophenyl)butyramides to 5-nitro-3,4-dihydro-1(2H)-naphthalenone is performed in substance or in an inert solvent in the presence of strong acids. Suitable solvents are linear, branched or cyclic aliphatic hydrocarbons, such as ligroin or cyclohexane, pentane, hexane, heptane, octane and aromatic solvents such as nitrotoluene. It is preferred to operate in substance or in ortho-nitrotoluene.

Suitable acids are strong Lewis or Bronsted acids, such as e.g. aluminium chloride, boron trifluoride, sulfuric acid, phosphoric acid, polyphosphoric acid, phosphorus pentoxide, methanesulfonic acid, trifluoromethanesulfonic acid, trifluoroacetic acid or mixtures of antimony pentafluoride and fluorosulfuric acid. Mixtures of these acids can also be used. Sulfuric acid or phosphoric acid is preferably used.

The acid is generally used in 0.1 to 100 mole equivalents, based on 4-(2-nitrophenyl)-butyric acid derivative. Preferably, 0.5 to 20 equivalents are used, particularly preferably 1 to 10 equivalents.

The reaction is generally carried out at temperatures of 0° C. to 150° C., preferably between 60° C. and 110° C.

The amination of 5-nitro-3,4-dihydro-1(2H)-naphthalenone to the nitro imine and/or nitro enamine takes place by reaction with ammonia, preferably in the presence of ammonium salts such as ammonium chloride.

The aromatisation or dehydrogenation of the nitro enamine 5-nitro-3,4-dihydro-1-naphthylamine or of the nitro imine 5-nitro-3,4-dihydro-1(2H)-naphthylimine to 5-nitro-1-naphthylamine or 5-nitroso-1-naphthylamine or a mixture of the compounds is carried out, e.g. in an inert solvent, in the presence of a catalyst. In addition to the dehydrogenated product 5-nitro-1-naphthylamine, 5-nitroso-1-naphthylamine formally resulting from symproportionation can also be produced in the process. 1,5-Naphthalenediamine is also formed in traces. The products can be further processed in any mixing ratios. Suitable solvents are ammonia and linear, branched or cyclic aliphatic hydrocarbons such as ligroin or cyclohexane, and also acetonitrile and aromatic solvents such as benzene, toluene, xylene, nitrobenzene, nitrotoluene or chlorobenzene. The aromatisation can also be performed in the absence of a solvent.

Suitable catalysts are dehydrogenation catalysts, which are described in the literature (Römpp Lexikon Chemie; Georg Thieme Verlag, Stuttgart, $10^{th}$ edition 1997, p. 891, chapter "Dehydrierung", $1^{st}$ section; Ullmann's Encyclopedia of Industrial Chemistry, VCH Verlagsgesellschaft mbH, Weinheim, $5^{th}$ edition 1989, vol. A13, chapter "Hydrogenation and Dehydrogenation", sub-chapter 2, "Dehydrogenation", p. 494–497). These include the metals of groups 8–10 of the periodic table (G. J. Leigh [editor], Nomenclature of Inorganic Chemistry, Recommendations 1990, Blackwell Scientific Publications, Oxford, Chapter I-3.8.1 "Groups of Elements in the Periodic Table and their Subdivision, p. 41–43), especially platinum, palladium, ruthenium and iridium, iron, cobalt, nickel and combinations thereof. The metals can also be used together with other metals, such as lanthanum, scandium, vanadium, chromium, molybdenum, tungsten, manganese, tin, zinc, copper, silver or indium. The above metals can be present as pure elements, as oxides, sulfides, halides, carbides or nitrides or can be used in combination with organic ligands. Suitable as ligands are hydrocarbon compounds with donor groups, such as e.g. amines, nitriles, phosphines, thiols, thioethers, alcohols, ethers or carboxylic acids. The catalysts are optionally applied to a support material. Suitable support materials are activated charcoal, aluminium oxide, silicon dioxide, zirconium oxide, zinc oxide or zeolites.

Work is optionally performed in the presence of an oxidising agent such as oxygen or air. The reaction is generally carried out at temperatures of 50° C. to 250° C., preferably at 100° C. to 200° C.

The subsequent hydrogenation of 5-nitro-1-naphthylamine or 5-nitroso-1-naphthyl-amine or a mixture of these compounds to 1,5-naphthalenediamine is performed as in step d) of the first preferred embodiment.

The process according to the invention based on ortho-nitrotoluene and acrylates and acrylamides can be illustrated in idealised form by the following reaction diagram:

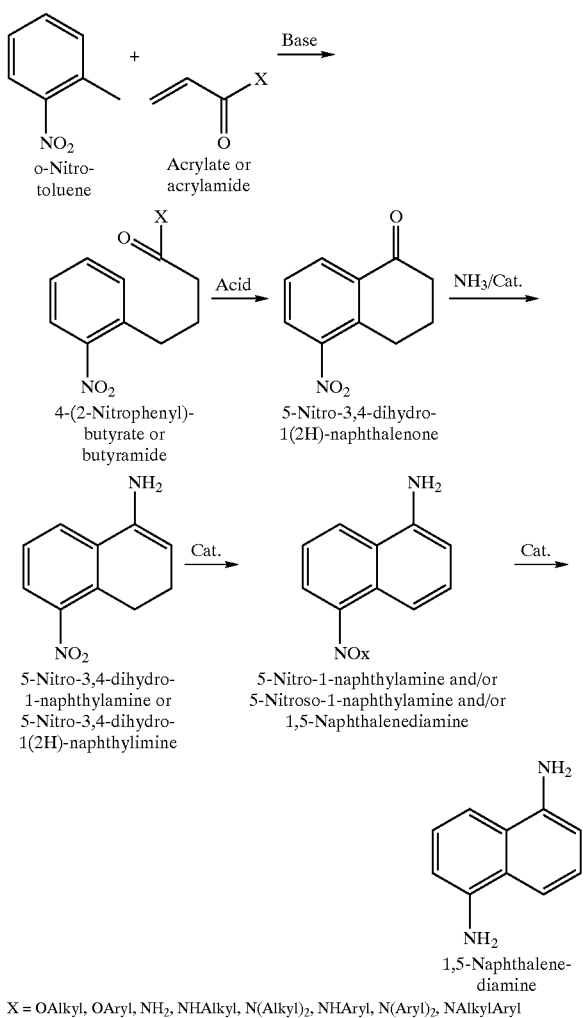

X = OAlkyl, OAryl, NH₂, NHAlkyl, N(Alkyl)₂, NHAryl, N(Aryl)₂, NAlkylAryl

The 1,5-naphthalenediamine can be phosgenated to give 1,5-naphthalene diisocyanate by a method that is known per se (DE-A1-19 651 041).

EXAMPLES

Embodiment 1

Example 1

Preparation of 4-(2-nitrophenyl)butyronitrile 0.75 ml of 45% sodium hydroxide solution and 175 mg of tributylmethylammonium chloride are placed in a 100 ml three-neck flask with a dropping funnel, reflux condenser and internal thermometer, stirring. At 40° C., a mixture of 1.4 ml acrylonitrile (21.15 mmol) and 25 ml ortho-nitrotoluene is added dropwise and maintained at this temperature for 3 h. The phases are separated, and the organic phase is dried and filtered off. With quantitative conversion of acrylonitrile, 1.61 g of 4-(2-nitro-phenyl)butyronitrile (8.5 mmol, 40%) are obtained.

Example 2

Preparation of 5-nitro-3,4-dihydro-1(2H)-naphthylimine 4 ml of concentrated sulfuric acid (75 mmol) are added to 107 mg of 4-(2-nitrophenyl)-butyronitrile (0.89 mmol) in a 50 ml glass round-bottomed flask under protective gas and the mixture is heated to 100° C. for 12 h. The cooled mixture is poured on to ice and immediately extracted with toluene. The yield of 5-nitro-3,4-dihydro-1(2H)-naphthyl-imine is 85% according to GC (area per cent).

Example 2a

Preparation of 5-nitro-3,4-dihydro-1(2H)-naphthalenone 1.00 g of fluorosulfuric acid (10 mmol) are added to 1.30 g of antimony(V) fluoride (6 mmol) in a 50 ml glass round-bottomed flask under protective gas and the mixture is cooled to 0° C. Then, 380 mg of 4-(2-nitrophenyl) butyronitrile (2 mmol) are added carefully. The mixture heats up to about 50° C. and is stirred for a farther 12 h at room temperature. The mixture is poured on to ice-cold sodium hydroxide solution, stirring is continued for 30 min at room temperature and then extraction is performed with toluene. Largely complete hydrolysis is made possible by the secondary stirring period. The organic phase is dried over sodium sulfate, filtered off and the solvent is distilled off under reduced pressure. The residue is purified by chromatography on silica gel (eluent cyclohexane/ethyl acetate 5:1 v/v). The yield of 5-nitro-3,4-dihydro-1(2H)-naphthalenone is 297 mg with a GC purity of 97% (76% of theoretical value).

Example 3

Preparation of 5-nitro-1-naphthylamine 1.0 g of 5-nitro-3,4-dihydro-1(2H)-naphthalenone (5.2 mmol), 5.2 mg of ammonium chloride (0.1 mmol) and 10.9 mg of ruthenium trichloride hydrate (0.05 mmol) are placed in a 0.1 liter autoclave. 10 ml of ammonia are condensed in, the autoclave is heated to 80° C. and then the pressure is increased to 200 bar with nitrogen. After stirring for 20 h under the above conditions, cooling takes place, the pressure is carefully released and the reaction mixture is dissolved out of the autoclave with 20 ml of dichloromethane. A mixture is obtained which contains, according to GC, in addition to 12% educt, 68% 5-nitro-3,4-dihydro-1-naphthylamine or 5-nitro-3,4-dihydro-1(2H)-naphthylimine, 17% 5-nitro-1-naphthylamine and traces of 1,5-naphthalene diamine (GC area percentages).

Example 4

Hydrogenation of 5-nitro-1-naphthylamine 8.20 g of 5-nitro-1-naphthylamine (43.6 mmol) in 35 ml of toluene are placed in a 0.1 liter autoclave with 0.5 g of palladium on carbon (5%) and hydrogenated at 50° C. and 40 bar hydrogen pressure for 5 h, stirring. On completion of the reaction, the cooled autoclave is depressurised and the catalyst is filtered off. With a quantitative conversion, 6.72 g of 1,5-naphthalenediamine (42.5 mmol, 97.5%) are formed.

Embodiment 2

Example 5

Synthesis of 4-(2-aminophenyl)butyronitrile 450 mg of 4-(2-nitrophenyl)butyronitrile, dissolved in 12.5 ml of methanol, are added dropwise to a mixture of 412 mg of iron powder (7.5 mmol) and 663 mg of ammonium chloride (12.5 mmol) in 12.5 ml of water at room temperature and under protective gas in a 100 ml glass round-bottomed flask. The mixture is heated for 5 hours with reflux. 25 ml of water are added to the cooled mixture and extraction is performed with toluene. The combined toluene phases are dried and the solvent distilled off under reduced pressure. The residue is purified by column chromatography on silica gel (eluent toluene/ethyl acetate 10:1 v/v). Yield: 276 mg (1.73 mmol, 72%).

Example 6

Synthesis of 5-amino-3,4-dihydro-1(2H)-naphthylimine

In a 50 ml glass flask, 380 mg of fluorosulfuric acid (3.8 mmol) are added dropwise to 122 mg of 4-(2-aminophenyl) butyronitrile (0.74 mmol) and 495 mg of antimony(V) fluoride (2.29 mmol), stirring, under argon and the mixture is heated to 100° C. for 4 hours. After cooling, the mixture is poured on to ice, directly neutralised with sodium hydroxide solution and extracted with toluene. The yield of 5-nitro-3,4-dihydro-1(2H)-naphthylimine is 77% according to GC. 5-Amino-3,4-dihydro-1(2H)-napthylimine can also be called 5-imino-5,6,7,8-tetrahydro-1-naphthylamine.

Example 6a

Synthesis of 5-amino-3,4-dihydro-1(2H)-naphthalenone

In a 50 ml glass flask, 380 mg of fluorosulfuric acid (3.8 mmol) are added dropwise to 122 mg of 4-(2-aminophenyl) butyronitrile (0.74 mmol) and 495 mg of antimony(V) fluoride (2.29 mmol), stirring, under argon and the mixture is heated to 100° C. for 4 hours. After cooling, the mixture is poured on to ice, neutralised with sodium hydroxide solution, stirred for 30 min at room temperature and extracted with toluene. As a result of the 30 min. secondary stirring period, largely complete hydrolysis is made possible. The yield of 5-amino-3,4-dihydro-1(2H)-naphthalenone is 64%.

Example 6b

Synthesis of 5-amino-3,4-dihydro-1(2H)-naphthalenone

In a 20 ml Schlenk vessel, 1 g of 96% sulfuric acid (9.79 mmol) is added to 100 mg of 4-(2-aminophenyl) butyronitrile (0.62 mmol) under argon. The mixture is heated to 100° C. for 66 h, stirring. After cooling, it is neutralised with aqueous ammonia solution (ice cooling), and the product is then extracted with chloroform and identified using GC.

Example 7

Synthesis of 1,5-naphthalenediamine from 5-amino-3,4-dihydro-1(2H)-naphthalenone 419.1 mg (2.6 mmol) of aminotetralon, 52 mg (0.97 mmol) of ammonium chloride and 230.5 mg (1.3 mmol) of palladium(II) chloride in 1 ml of acetonitrile are placed in a 0.1 liter stainless steel autoclave. 5 ml of ammonia are added, the mixture is heated to 130° C. and then the pressure is increased to 200 bar with nitrogen. It is stirred under the above reaction conditions for 20 h and then cooled to room temperature and the pressure is slowly released. The residue is dissolved in a mixture of acetonitrile, toluene and dichloromethane, filtered over sodium sulfate and then the solvent is removed under vacuum.

Yield: 321 mg (78%).

Embodiment 4

Example 8

Synthesis of 5-amino-3,4-dihydro-1(2H)-naphthalenone from 5-nitro-3,4-dihydro-1(2H)-naphthalenone 9.18 g of iron powder and 16.64 g of ammonium chloride in 274 ml of water are placed in a 1-liter, four-neck flask. 10 g of 5-nitro-3,4-dihydro-1(2H)-naphthalenone (52.4 mmol) dissolved in 550 ml of methanol are added dropwise, stirring, over 3.5 hours at 25° C. On completion of the dropwise addition, heating is performed with reflux for 3.5 hours. After cooling, the pH is adjusted to pH 11 with aqueous ammonia solution (25%). The product is extracted from the aqueous phase with chloroform, dried over sodium sulfate and concentrated under vacuum. The product is obtained as a reddish-brown solid in an 81% yield (6.8 g).

Embodiment 5

Example 9

Synthesis of 4-(2-nitrophenyl)methyl butyrate

A mixture of 400 g (2.92 mol) of ortho-nitrotoluene and 12.7 g (0.148 mol) of methyl acrylate is added to a mixture of 14.4 g of 67% potassium hydroxide solution and 1.7 g of tetrabutylammonium chloride at 40° C. and the mixture is stirred for 1 h. The mixture is neutralised with 30% sulfuric acid and the phases are separated. According to GC analysis with an internal standard, the yield is 50%.

The organic phases of 4 identical tests are combined and dried over $Na_2SO_4$. Under a pressure of 0.1 bar, excess nitrotoluene is distilled off up to an overhead temperature of 110° C. At an overhead temperature of 120–130° C., 59.1 g (265 mmol) of 4-(2-nitrophenyl)methyl butyrate are obtained with a purity of approx. 98%. The isolated yield corresponds to 45%.

Example 10

Synthesis of 5-nitro-3,4-dihydro-1(2H)-naphthalenone 100 mg (0.45 mmol) of 4-(2-nitrophenyl)methyl butyrate are dissolved in 1.68 g of trifluoromethanesulfonic acid and heated to 100° C. for 24 h. 5 ml of water and 5 ml of toluene are carefully added to the cooled reaction mixture. The phases are separated and the organic phase investigated by gas chromatography with an internal standard. The yield of 5-nitro-3,4-dihydro-1(2H)-naphthalenone is 81%.

Example 10a

Synthesis of 5-nitro-3,4-dihydro-1(2H)-naphthalenone 250 mg (1.12 mmol) of 4-(2-nitrophenyl)methyl butyrate are dissolved in 5.49 g of 98% sulfuric acid and heated to 100° C. for 24 h. 5 ml of water and 5 ml of toluene are carefully added to the cooled reaction mixture. The phases are separated and the organic phase investigated by gas chromatography with an internal standard. The yield of 5-nitro-3,4-dihydro-1(2H)-naphthalenone is 42%.

What is claimed is:

1. Process for the production of 1,5-naphthalenediamine containing a step in which ortho-nitrotoluene is reacted with one or more acrylic acid derivatives.

2. Process according to claim 1 in which methyl acrylate, ethyl acrylate, butyl acrylate or acrylamide is used as the acrylic acid derivative.

3. Process according to claim 1, containing a step in which ortho-nitrotoluene is reacted with acrylonitrile to give 4-(2-nitrophenyl)butyronitrile.

4. Process for the production of 1,5-naphthalenediamine according to claim 3, containing the steps a) reaction of ortho-nitrotoluene with acrylonitrile to give 4-(2-nitrophenyl)butyronitrile, b) cyclisation of the 4-(2-nitrophenyl)butyronitrile formed in step a) to the nitro imine and/or nitro enamine, c) aromatisation of the nitro imine and/or nitro enamine formed in step b) to give 5-nitro-1-naphthylamine and/or 5-nitroso-1-naphthylamine, d) hydrogenation of the 5-nitro-1-naphthylamine and/or 5-nitroso-1-naphthylamine formed in step c) to give 1,5-naphthalenediamine.

5. Process according to claim 4, in which the nitro imine and/or nitro enamine formed in step b) is first converted to the nitroketone 5-nitro-3,4-dihydro-1(2H)-naphthalenone, the nitroketone is then isolated, then converted back to the nitro imine and/or nitro enamine, and then aromatised in step c).

6. Process for the production of 1,5-naphthalenediamine according to claim 3, containing the steps a) reaction of ortho-nitrotoluene with acrylonitrile to give 4-(2-nitrophenyl)-butyronitrile, b) reduction of the 4-(2-nitrophenyl)butyronitrile formed in step a) to give 4-(2-aminophenyl)butyronitrile, c) cyclisation of the 4-(2-aminophenyl)butyronitrile formed in step b) to the amino imine and/or amino enamine, d) aromatisation of the amino imine and/or amino enamine formed in step c) to give 1,5-naphthalenediamine.

7. Process according to claim 6, in which the amino imine and/or amino enamine formed in step c) is first converted to the aminoketone 5-amino-3,4-dihydro-1(2H)-naphthalenone, the aminoketone is then isolated, then converted back to the amino imine and/or amino enamine and then aromatised in step d).

8. Process for the production of 1,5-naphthalenediamine according to claim 3, containing the steps a) reaction of ortho-nitrotoluene with acrylonitrile to give 4-(2-nitrophenyl)-butyronitrile, b) cyclisation of the 4-(2-nitrophenyl)butyronitrile formed in step a) to the nitro imine and/or nitro enamine, c) reduction of the nitro imine and/or nitro enamine formed in step b) to give the amino imine and/or amino enamine, d) aromatisation of the amino imine and/or amino enamine formed in step c) to give 1,5-naphthalenediamine.

9. Process for the production of 1,5-naphthalenediamine according to claim 3, containing the steps a) reaction of ortho-nitrotoluene with acrylonitrile to give 4-(2-nitrophenyl)-butyronitrile, b) cyclisation of the 4-(2-nitrophenyl)butyronitrile formed in step a) to the nitro imine and/or nitro enamine, conversion to the nitroketone 5-nitro-3,4-dihydro-1(2H)-naphthalenone, and isolation of the nitroketone, c) reduction of the nitroketone 5-nitro-3,4-dihydro-1(2H)-naphthalenone formed in step b) to give the aminoketone 5-amino-3,4-dihydro-1(2H)-naphthalenone, d) conversion of the aminoketone formed in step c) to the amino imine 5-amino-3,4-dihydro-1(2H)-naphthylimine and/or amino enamine 5-amino-3,4-dihydro-1-naphthylamine and aromatisation to give 1,5-naphthalenediamine.

10. Process for the production of 1,5-naphthalenediamine according to claim 1, containing the steps a) reaction of ortho-nitrotoluene with an acrylate or acrylamide to give 4-(2-nitrophenyl)butyrate or 4-(2-nitrophenyl)butyramide, b) cyclisation of the butyrate or butyramide formed in step a) to give 5-nitro-3,4-dihydro-1(2H)-naphthalenone, c) amination of the 5-nitro-3,4-dihydro-1(2H)-naphthalenone formed in step b) to give 5-nitro-3,4-dihydro-1-naphthylamine or the tautomeric 5-nitro-3,4-dihydro-1(2H)-naphthylimine, d) aromatisation of the 5-nitro-3,4-dihydro-1-naphthylamine or the tautomeric 5-nitro-3,4-dihydro-1(2H)-naphthylimine formed in step c) to give 5-nitro-1-naphthylamine and/or 5-nitroso-1-naphthylamine, e) hydrogenation of the 5-nitro-1-naphthylamine and/or 5-nitroso-1-naphthylamine formed in step d) to give 1,5-naphthalenediamine.

11. Process for the production of 1,5-naphthalene diisocyanate in which 1,5-naphthalenediamine, produced in accordance with one of claims 1 to 10, is phosgenated.

* * * * *